United States Patent [19]
Failli

[11] Patent Number: 4,822,893
[45] Date of Patent: Apr. 18, 1989

[54] PRODUCTION OF SUBSTITUTED 1,3,4,9-TETRAHYDROPYRANO[3,4-B]INDOLE-1-ACETIC ACIDS

[75] Inventor: Amedeo A. Failli, Princeton Junction, N.J.

[73] Assignee: American Home Products, New York, N.Y.

[21] Appl. No.: 153,167

[22] Filed: Feb. 8, 1988

[51] Int. Cl.$^4$ .......................................... C07D 493/04
[52] U.S. Cl. .................................................... 548/432
[58] Field of Search ...................... 548/432, 508, 494; 564/251, 314, 417, 418

[56] References Cited

U.S. PATENT DOCUMENTS

| | | | |
|---|---|---|---|
| 3,843,681 | 10/1974 | Demerson et al. | 548/432 |
| 3,939,178 | 2/1976 | Demerson et al. | 548/432 |
| 3,974,179 | 8/1976 | Demerson et al. | 548/432 |
| 4,585,877 | 4/1986 | Demerson et al. | 548/432 |
| 4,670,462 | 6/1987 | Katz et al. | 548/432 |

Primary Examiner—Mary E. Ceperley
Attorney, Agent, or Firm—Walter Patton

[57] ABSTRACT

Process for the production of substituted 1,3,4,9-tetrahydropyrano[3,4-b]indole-1-acetic acid having useful analgesic and anti-inflammatory activity.

15 Claims, No Drawings

PRODUCTION OF SUBSTITUTED 1,3,4,9-TETRAHYDROPYRANO[3,4-b]INDOLE-1-ACETIC ACIDS

BACKGROUND OF THE INVENTION a. Field of Invention

This invention relates to novel processes for the production of indole derivatives.

More specifically, this invention relates to the process for the production of tricyclic acetic acid derivatives in which the tricyclic portion thereof is characterized by having an indole portion fused to a pyrano ring. Still more specifically, the process of this invention produces the following tricyclic acetic acid system:

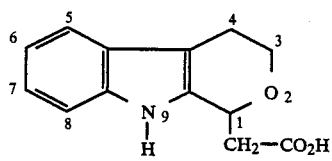

designated 1,3,4,9-tetrahydropyrano[3,4-b]indole-1-acetic acid in which the carbons at the 1-, 7- and 8-positions and optionally at the 4-, 5- and 6-positions are further substituted.

The indole derivatives produced by the present process are described in U.S. Ser. No. 117,775, filed Nov. 5, 1987, now U.S. Pat. No. 4,785,015 and which is herein incorporated by reference.

The indole derivatives produced by the present process are known to exhibit useful pharmacodynamic properties without eliciting undesireable side effects. Notable attributes of these derivatives are anti-inflammatory and analgesic activities.

b. Prior Art

The closest prior art to the present invention is: McKittrick et al, U.S. Ser. No. 117,775, filed Nov. 5, 1987, now U.S. Pat. No. 4,785,015; C. Shaw et al, U.S. Ser. No. 089,881, filed Aug. 27, 1987; and Demerson et al, U.S. Pat. No. 3,939,178. Demerson et al disclosed the production of 1,3,4,9-tetrahydropyrano[3,4-b]indoles and 1,3,4,9-tetrahydrothiopyranol[3,4-b]indoles having analgesic and anti-inflammatory activity. Related U.S. Patents are U.S. Pat. Nos. 3,974,179; 3,848,681; and 4,670,462.

SUMMARY OF THE INVENTION

The process of the present invention is directed to the production of the compounds represented by formula (I)

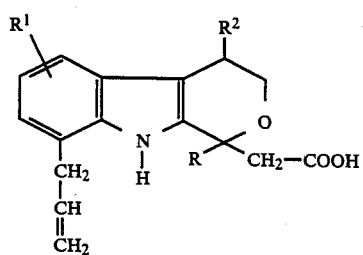

wherein R is lower alkyl containing 1 to 4 carbon atoms; $R^1$ is hydrogen, lower alkyl containing 1 to 4 carbon atoms, or halogen; $R^2$ is hydrogen or lower alkyl containing 1 to 4 carbon atoms and the pharmaceutically acceptable salts thereof.

The term "lower alkyl" as used herein represents straight chain alkyl radicals containing 1 to 4 carbon atoms and branched chain alkyl radicals containing 2 to 4 carbon atoms and includes methyl, ethyl, butyl, isobutyl and the like.

The term "halogen" as used herein includes fluorine, chlorine, bromine and iodine.

The preferred process of the present invention is directed to the production of the compound designated 1-ethyl-7-fluoro-1,3,4,9-tetrahydro-8-(2-propenyl)-pyrano[3,4-b]indole-1-acetic acid, and the pharmaceutically acceptable salts thereof.

A still further preferred aspect of the present invention is directed to the production of 1-ethyl-1,3,4,9-tetrahydro-8-(2-propenyl)pyrano[3,4-b]indole-1-acetic acid; and 1-ethyl-1,3,4,9-tetrahydro-4-methyl-8-(2-propenyl)pyrano[3,4-b]indole-1-acetic acid (Isomer A) and the pharmaceutically acceptable salts thereof.

The processes of the present invention are represented by the following flow sheets:

Process A

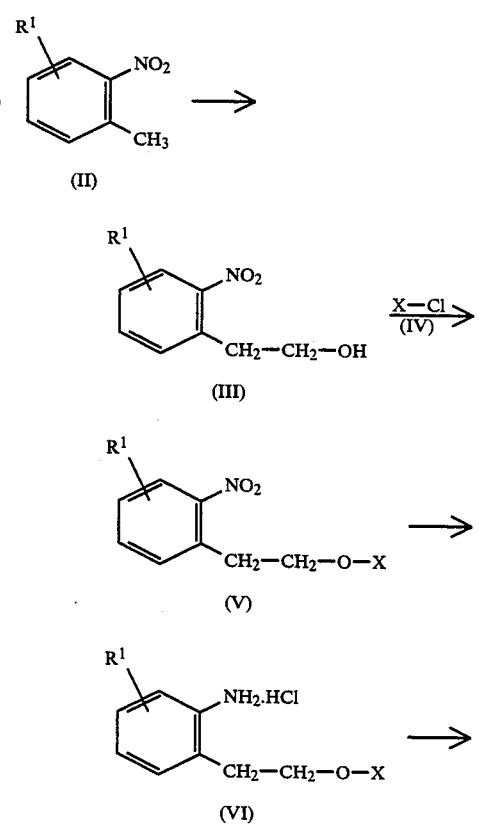

Process A
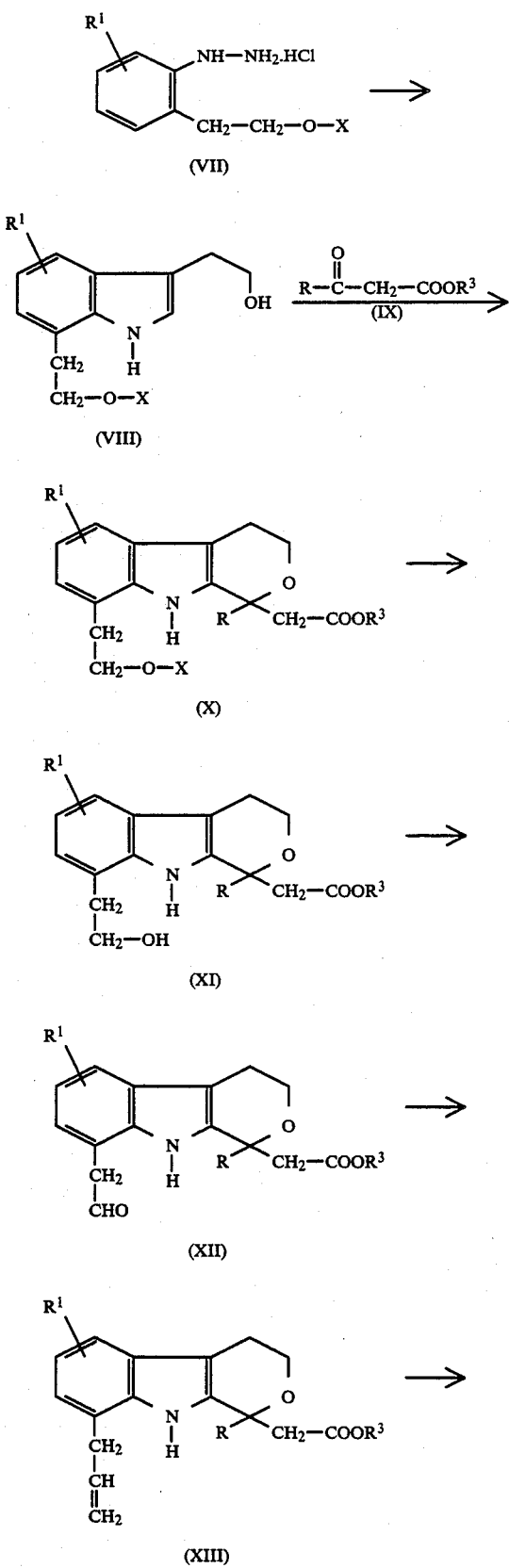
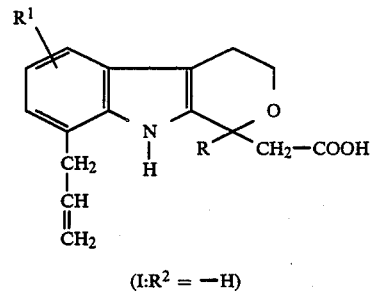
wherein R and R[1] are as defined above; R[3] is lower alkyl containing 1 to 8 carbon atoms and X is benzyl or similar protecting group.
Process B
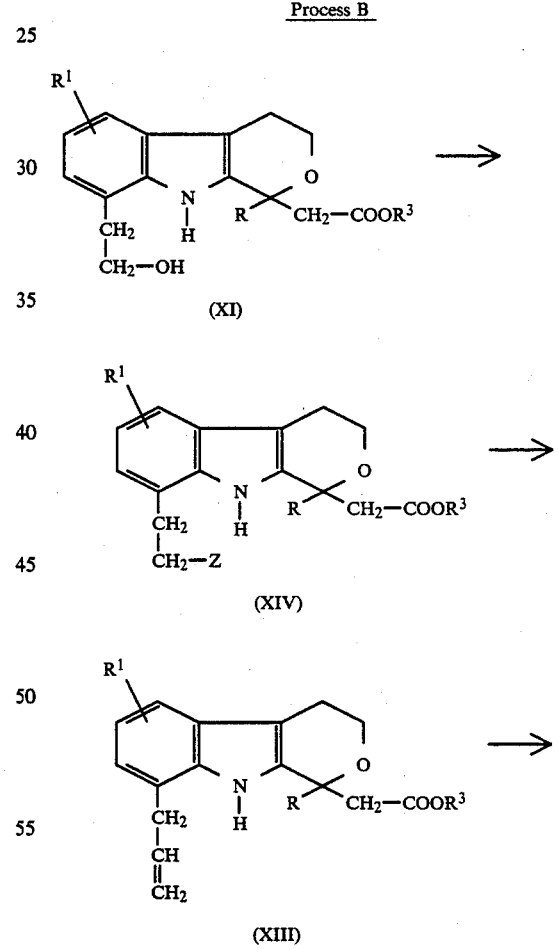
continue as in Process A to produce (I:R[2] = —H)
wherein R, R[1] and R[3] are as defined above and Z is chlorine, bromine or iodine.

Process C

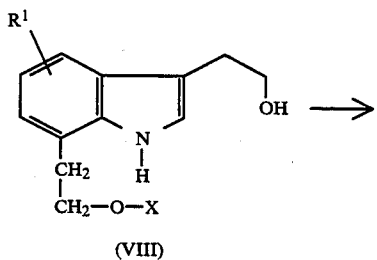

(VIII)

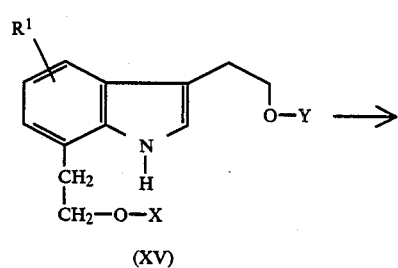

(XV)

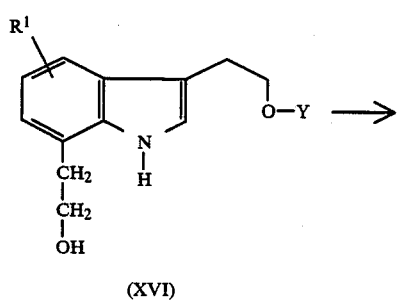

(XVI)

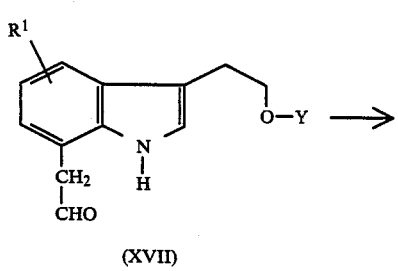

(XVII)

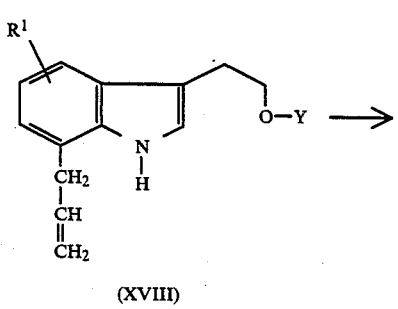

(XVIII)

-continued
Process C

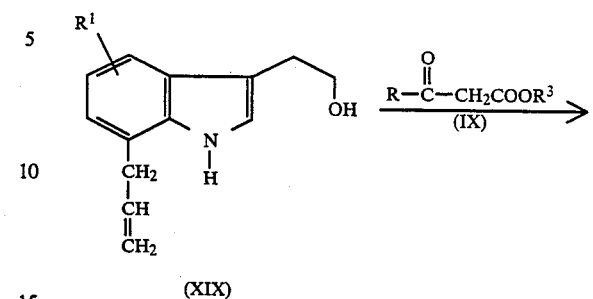

(XIX)

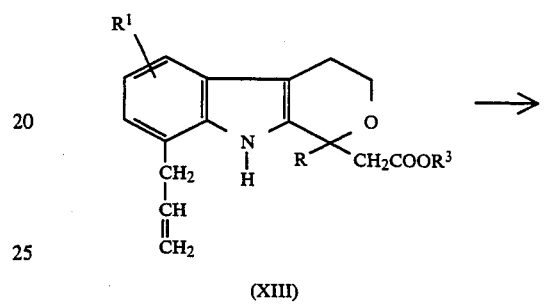

(XIII)

continue as in Process A to produce (I:R$^2$ = —H)

wherein R, R$^1$, R$^3$ and X are as defined above and Y is acetyl or similar protecting group.

Process D

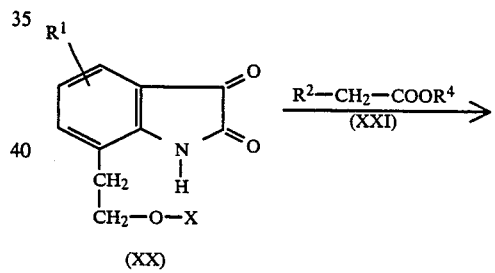

(XX)

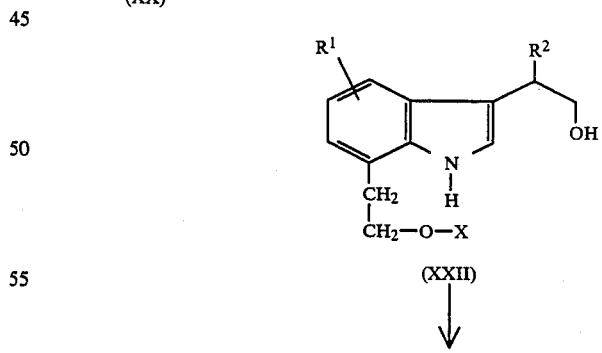

(XXII)

continue as in Process A to produce (I)

wherein R$^1$, R$^2$ and X are as defined above and R$^4$ is methyl or ethyl.

Referring to Process A, the substituted 2-nitrotoluene (II) was directly homologated at the benzylic position in high yield by treatment with one equivalent of paraformaldehyde and a catalytic amount of KOH in ethanol according to L. Florvall et al, J. Med. Chem. 29, 1406, 1986.

The alkylation of the crude intermediate alcohol (III) was carried out either with benzyl bromide and potassium tert-butoxide in THF at 0° C. or preferably with a large excess of benzyl chloride in the presence of 50% aqueous NaOH and a phase transfer catalyst such as tetra-n-butylammonium iodide or hydrogen sulfate. Reduction of the nitro compound (V) was accomplished in high yield with sodium polysulfide in refluxing ethanol according to L. Florvall et al, J. Med. Chem. 29, 1406, 1986.

Acidification of the extracts prior to removal of the solvent yielded the crystalline aniline hydrochloride (VI) which was freed of impurities by simple ether trituration.

Diazotization of the aniline (VI) followed by reduction of the diazonium salt with tin (II) chloride dihydrate at −10° C. proceeded to give a high yield of the hydrazine hydrochloride (VII). At higher temperatures a gum was readily formed which resulted in unreacted starting material and considerably lower yields of impure product.

The said hydrazine was condensed with 2,3-dihydrofuran and the crude hydrazone cyclized to the substituted tryptophol (VIII). Although the cyclization could be carried out with a variety of mineral or Lewis acids it was conveniently carried out thermally with anhydrous zinc chloride as the catalyst.

Production of the ester (X) was preferably done by stirring a mixture of the tryptophol (VIII) and the 3-oxo-2-alkanoic acid alkyl ester of formula (IX) or preferably its enolether at room temperatures in toluene. The yield was virtually quantitative when one equivalent of boron trifluoride etherate was employed as the catalyst. With less than one equivalent of catalyst lower yields (43–46%) resulted despite prolonged reaction times.

Removal of the benzyl protecting group from (X) was effected by either catalytic transfer hydrogenation (i.e. cyclohexadiene, 10% Pd-C, ethanol, 50° C. or cyclohexadiene, acetic acid, Pd black, 85° C.) or by hydrogenation under medium pressure (50 psi, 10% Pd-C) in methanol or acetic acid. However, it was preferably carried out by hydrogenolysis at atmospheric pressure and room temperature using 10% Pd-C in a 3:1 mixture of methanol and acetic acid. Under these conditions a quantitative yield of (XI) was obtained free of unreacted starting material or products of overreduction (i.e. indolines) sometimes observed under transfer hydrogenation or medium pressure hydrogenation, respectively.

Oxidation of the crude alcohol (XI) to the aldehyde (XII) could be effected by a variety of chromium based or DMSO activated oxidizing reagents such as Collins reagent (J. C. Collins et al, Tetr. Letters 30, 3363, 1968) or the Pfitzner-Moffatt oxidation (J. Am. CHem. Soc. 87, 5661 and 5670, 1965). However, it was preferably carried out in a very efficient and simple manner with Dess-Martin periodinane (1.3–1.5 equivalents, in dichloromethane at room temperature).

Olefination of the crude aldehydes ester (XII) to yield (XIII) was accomplished by Wittig reaction of (XII) with the ylid generated in situ from a methyl triphenylphosphonium salt (chloride, bromide or iodide) with either phenyllithium or n-butyllithium or sodium amide as the base at room temperature or below. Phase transfer conditions, such as the use of potassium carbonate and 18-crown-6 in ether or THF were also found to be useful in minimizing competing aldolization reactions that tend to occur with stronger bases.

Alternatively, olefination of (XII) without contamination with isomeric olefins occurred via the acid promoted elimination of a β-hydroxy alkylsilane resulting from treatment of (XII) with trimethylsilyl methyl magnesium chloride (Peterson olefination).

However, the said olefination was preferably carried out by a mild, nonbasic procedure involving the reaction of (XII) with the highly reactive, electrophilic reagent prepared from zinc dust, methylene bromide and THF with added TiCl$_4$ as described by L. Lombardo, Tetr. Letters, 23, 4293, 1982 and Org. Syntheses, 65, 81, 1987. Best yields were obtained by carrying out the reaction at room temperature or below. Its nonbasic character together with its compatibility with a variety of functional groups including acids and esters, makes this reagent uniquely suited for the direct conversion of (XII) to (XIII).

The product (XIII) was subjected to basic hydrolysis (i.e. 1N NaOH or K$_2$CO$_3$ or preferably 1N LiOH in aqueous alcohol, preferably at room temperature) and upon acidification the product (I) was obtained in high yield. The final purification of (I) was carried out by recrystallization from dichloromethane-hexane and afforded a material with a lower overall impurity content than hitherto available. In addition, the present process has the following advantages:

it maximizes the use of crude or minimally purified intermediates the overall yield of the 10 step synthesis is a high 14.2% of theory it does not require specialized techniques such as low temperature lithiations or pressure requiring organometallic reactions uses simple protection/deprotection steps (i.e. benzylation/debenzylation) for ease of operation and most steps require a minimum turn around time uses reagents that are commercially available or economically prepared or easy to regenerate and recycle it is readily adaptable to scale up.

Referring to Process B, in the reaction of the alcohol (XI) with, for example, SOCl$_2$ in toluene or PBr$_3$ in ether or dichloromethane good yields of the corresponding halides of structure (XIV) were obtained. Further reaction of these halides with triphenylphosphine provided the corresponding triphenylphosphonium salts which were then condensed with formaldehyde under standard Wittig conditions to yield the olefinic ester (XIII). This ester produced by Process B was converted to the final product (I) by the Process A.

In the alternate Process C the substituted tryptophol (VIII) was first protected with an acetyl or similar group that allowed selective removal of the already present benzyl protecting group. Removal of the latter protecting group could be carried out by catalytic transfer hydrogenation (cyclohexene, 10% Pd-C,- refluxing methanol) or medium pressure hydrogenation (10% Pd-C 50 psi in methanol or preferably acetic acid). However, higher yields of cleaner product (XVI) were obtained by hydrogenolysis at atmospheric pressure and room temperature using 10% Pd-C in a 3:1 mixture of methanol and acetic acid.

The alcohol (XVI) was then oxidized to the aldehyde (XVII) and the latter methylenated to give the olefin (XVIII) under conditions essentially identical to those used in Process A to convert the alcohol (XI) to the olefinic ester (XIII).

Removal of the acetyl protecting group (mild basic hydrolysis) yielded the substituted tryptophol (XIX) which was cyclized to the pyrano ester (XIII) under conditions essentially identical to those used in Process A to obtain the ester (X) from the tryptophol (VIII).

The crude ester (XIII) produced in Process C was then converted into the final product (I) by the Process A.

Referring to Process D the alkylation of the substituted isatin (XX) with methyl or ethyl propionate (XXI) followed by reduction of the resulting adduct with lithium aluminum hydride or preferably with the safe and inexpensive sodium borohydride and boron trifluoride etherate reagents according to C. Shaw et al, U.S. Ser. No. 089,881, filed Aug. 27, 1987, proceeded to give the substituted tryptophol (XXII) in good yield. The tryptophol (XXII) produced by Process D was converted to the final product (I) by the Process A.

The compounds of formula (I) form salts with suitable pharmaceutically acceptable inorganic and organic bases. The acid of formula (I) is transformed in excellent yield into the corresponding pharmaceutically acceptable salts by neutralization of said acid with the appropriate inorganic or organic base. Suitable inorganic bases to form these salts include, for example, the hydroxides, carbonates, bicarbonates, or alkoxides of the alkali metals, or alkaline earth metals, for example, sodium, potassium, magnesium, calcium, and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; cyclic saturated or unsaturated bases containing up to six carbon atoms, such as pyrrolidine, piperidine, morpholine, piperazine, and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol, and trimethyl-monoethanol) and cyclic ammonium salts, for example the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by good water-solubility.

In principle, however, there can be used all the ammonium salts which are physiologically compatible.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Preferably, the reaction is performed in a water-miscible organic solvent inert to the reaction conditions, for example, methanol, ethanol, dioxane, and the like in the presence of water. For example, such use of sodium hydroxide, sodium carbonate, or sodium bicarbonate gives a solution of the sodium salts. Evaporation of the solution or addition of a water-miscible solvent of a more moderate polarity, for example, a lower alkanol, for instance, butanol, or a lower alkanone, for example, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether, or benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Included in the present invention is the process for the production of diastereoisomers of compound (I) wherein the 4-substituent is either cis or trans to the acetic acid chain at position one.

Also included in this invention is the process for the resolution of the compounds of formula (I) into their optical isomers. The optical isomers of the compounds of formula (I) result from asymmetric centers, contained therein. Such isomers can be obtained in substantially pure form by classical separation techniques and by sterically controlled synthesis. Included is the specific case of the resolution of 1-ethyl-7-fluoro-1,3,4,9-tetrahydro-(8-(2-propenyl)pyrano[3,4-b]indole-1-acetic acid into its optical isomers by separation of the corresponding [(1S)-endo]-1,7,7-trimethyl-bicyclo[2.2.1]heptan-2-yl ester followed by basic hydrolysis.

The following examples further illustrate the present invention.

EXAMPLE 1

Process A

Preparation of 2-Fluoro-6-nitrophenethyl Alcohol (III: $R^1=2$-F)

According to the procedure of L. Florvall et al. J. Med. Chem. 29, 1406 (1986), a solution of KOH (0.75 g) in ethanol (5 mL) was added to a mixture of 2-fluoro-6-nitrotoluene (77.5 g, 0.5 mole) and paraformaldehyde (15 g, 0.5 mole) in DMSO (75 mL). The dark solution was stirred for 3 days at room temperature, diluted with water (1.2 L), neutralized with 2.5N HCl (to pH 6.5) and extracted with ether (3×). The extracts were washed with brine (1×), dried (MgSO$_4$) and evaporated to dryness to yield a yellow solid. Trituration with light petroleum ether removed a small amount of unreacted starting material and provided 2-fluoro-6-nitrophenethyl alcohol as a pale yellow solid, 82.3 g, 89.3%, m.p. 42°–44° C. This material was used for the subsequent reaction without further purification. An analytical sample was purified by flash chromatography (silica Merck-60, hexane-ether 6:4), m.p. 45°–46° C.

$^1$H NMR (400 MHz, CDCl$_3$): δ1.67 (t, J=6 Hz, 1H, OH), 3.2 (t, J=7 Hz, 2H, CH$_2$Ph), 3.93 (m, 2H, CH$_2$O), 7.37 (m, 2H, ArH), 7.72 (d, J=7 Hz, 1H, ArH).

EXAMPLE 2

Process A

Preparation of 2-(2-Benzyloxyethyl)-3-fluoronitrobenzene (V: $R^1=3$-F, X=—CH$_2$Ph)

50% NaOH (133 mL) was added slowly with ice cooling to a mechanically stirred mixture of 2-fluoro-6-nitrophenethyl alcohol (82 g, 0.44 mole) and benzyl chloride (300 mL). Following the addition of tetra-n-butyl ammonium hydrogen sulfate (7.5 g) the cooling bath was removed. After about 15 minutes the mixture became dark red and the temperature rose. Occasional cooling was needed to maintain it at 30°–35° C. After 30 minutes no starting material was present by TLC (silica, dichloromethane). After an additional 15 minutes the mixture was diluted with ice-cold water (300 mL) and extracted with ether (3×). The extracts were washed with brine, dried (MgSO$_4$) and the volatiles removed in vacuo (water aspirator) at 45° C. (bath temperature). The residue (light orange oil) was dissolved in hexane and adsorbed on a 4 inch column of flash silica gel (5½ inches in diameter). The less polar impurities were washed out with hexane. Further washing with hexane-dichloromethane or hexane-ethyl acetate (1:1) yielded 116.8 g (95.6%) of the title product. This material was used for the subsequent reaction without further purification.

$^1$H NMR (400 Mhz, CDCl$_3$): δ3.26 (t, J=7 Hz, 2H, PhCH$_2$C), 3.70 (t, J=7 Hz, 2H, CCH$_2$O), 4.50 (s, 2H, OCH$_2$Ph), 7.29 (m, 7H, ArH), 7.68 (d, J=8 Hz, ArH).

MS (m/z, CI): 276 (M+H)$^+$, 168 (M-PhCH$_2$O)$^+$, 91.

EXAMPLE 3

Process A

Preparation of 2-(2-Benzyloxyethyl)-3-fluoroaniline Hydrochloride (VI: $R^1=3$-F, X=CH$_2$Ph)

According to the procedure of L. Florvall et al, J. Med. Chem. 29, 1406, (1986) a mixture of sodium sulfide nonahydrate (92.57 g, 0.385 mole, note: large lumps were crushed in a mortar prior to use), sulfur (sublimed, 12.35 g, 0.385 mole), water (194 mL) and ethanol (97 mL) was mechanically stirred until an orange solution was obtained (about 15 minutes). A solution of 2-(2-benzyloxyethyl)-3-fluoronitrobenzene (53 g, 0.192 mole) in ethanol (40 mL) was added dropwise (over 15 minutes). The mixture was then refluxed for 3 hours under a nitrogen blanket. Upon cooling the ethanol was evaporated and the residue diluted with water (500 mL) and extracted with ether (3×). The extracts were washed with brine, dried (MgSO$_4$) and concentrated to a small volume. Careful acidification (to pH 3) with anhydrous ethereal HCl yielded the title compound as the hydrochloride salt. The crude material was collected, washed with ether and dried to provide white needles (44.3 g, 82.03%, m.p. 147°–149° C.). This material was used for the subsequent reaction without further purification.

$^1$H NMR (400 MHz, DMSO-d$_6$): δ2.95 (t, J=6 Hz, 2H, ArCH$_2$C), 3.60 (t, J=7 Hz, 2H, CCH$_2$O), 4.48 (s, 2H, OCH$_2$Ph), 6.93 (t, J=9 Hz, 1H, ArH), 7.04 (d, J=8 Hz, 1H, ArH), 7.27 (m, 6H, ArH).

MS (m/z, EI): 245 (M)$^+$, 154 (M-PhCH$_2$)$^+$, 124 (M-PhCH$_2$OCH$_2$, b.p.)$^+$, 91.

Anal. Calcd. for C$_{15}$H$_{16}$FNO.HCl: C, 63.94; H, 6.08; N, 4.97%. Found: C, 63.51; H, 6.00; N, 5.29%.

EXAMPLE 4

Process A

Preparation of 2-(2-Benzyloxyethyl)-3-fluorophenylhydrazine Hydrochloride (VII: $R^1=3$-F, X=CH$_2$Ph)

A mechanically stirred suspension of 2-(2-benzyloxyethyl)-3-fluoroaniline hydrochloride (53 g, 0.188 mole) in a mixture of water (30 mL), concentrated HCl (127 mL) and glacial HOAc (127 mL) was cooled to −10° C. (internal temperature). A solution of NaNO$_2$ (14.27 g, 0.206 mole) in water (52 mL) was added dropwise while maintaining the internal temperature at −10° C. The resulting red solution was stirred an additional 75 minutes at −10° C. and then treated dropwise (over 30 minutes) with a solution of tin (II) chloride dihydrate (84.8 g, 0.376 mole) in concentrated HCl (97 mL) precooled to −40° C. The mixture was stirred an additional 75 minutes at −10° C. and then cooled at −15° C. and basified (to pH 14) with 50% NaOH (about 320 mL). The internal temperature was kept at −8°/−10° C. during the addition of the base. The mixture was extracted with ether (3×). The combined extracts were washed with brine, dried (anhydrous K$_2$CO$_3$) and carefully acidified with ethereal HCl. Removal of the solvent provided the title compound as a tan solid (54 g, 96.9%). Trituration with light petroleum ether removed the less polar impurities and provided pure product (48.4 g, 86.8%).

$^1$H NMR (400 MHz, DMSO-d$_6$): δ2.92 (t, J=6.5 Hz, 2H, ArCH$_2$C), 3.55 (t, J=7 Hz, 2H, CCH$_2$O), 4.48 (s, 2H, OCH$_2$Ph), 6.8 (m, 6H, PhH+ArH), 8.12 (broad, 1H, NH), 10.27 (broad, 3H, NH$_3$).

MS (m/z): 260 (M)$^+$, 169 (M-PhCH$_2$)$^+$, 91 (b.p., C$_7$H$_7$)$^+$.

EXAMPLE 5

Process A

Preparation of 6-Fluoro-7-(2-benzyloxyethyl)tryptophol (VIII: R$^1$=6-F, X=—CH$_2$Ph)

Step 1. Preparation of 4-[2-(2-Benzyloxyethyl)-3-fluorophenylhydrazono]-1-butanol 2-(2-Benzyloxyethyl)-3-fluorophenylhydrazine hydrochloride (48.4 g, 0.1632 mole) was dissolved with stirring in a mixture of THF (440 mL) and water (60 mL). The dark solution was cooled to −10° C. (external temperature) and treated with a solution of 2,3-dihydrofuran (11.43 g, 0.1632 mole) in THF (40 mL). The mixture was allowed to warm to room temperature. After stirring for 2 hours the reaction was virtually complete as shown by TLC (silica, CH$_2$Cl$_2$CH$_3$OH 99:1; UV, Vaughn's). After stirring overnight the mixture was diluted with ether (400 mL) and brine (150 mL). The organic phase was washed with brine, dried (MgSO$_4$) and evaporated to dryness to yield the crude hydrazone (thick reddish oil, quantitative yield, mixture of E/Z isomers). The crude material was used for the subsequent reaction without further purification.

MS (m/z, EI): 330 (M+), 91 (b.p.).

Step 2. Preparation of 6-Fluoro-7-(2-benzyloxyethyl)tryptophol

Under a nitrogen atmosphere, a mixture of the crude hydrazone (0.1632 mole) and zinc chloride (51 g, 0.374 mole) in ethylene glycol (210 mL) was heated slowly in an oil bath to 90° C. and kept at this temperature until homogeneous (15–20 minutes). The temperature of the bath was then raised to 155° C. After stirring for two hours at this temperature the reaction was virtually complete (TLC, silica, hexane-ethyl acetate 1:1). The mixture was cooled and poured into 1N-HCl (330 mL) containing crushed ice (330 mL) and extracted with ether and ethyl acetate. The combined extracts were washed with brine and dried (MgSO$_4$). Removal of the solvent yielded a brown oil which was dissolved in methylene chloride and adsorbed on a short column of flash silica gel (4 inch diameter, packed dry). Elution with dichloromethane followed by hexane-ethyl acetate 1:1 provided pure title compound as a tan solid (23.72 g, 46.4%, m.p. 75°–77° C. with softening and decomposition).

$^1$H NMR (400 MHz, CDCl$_3$): δ2.98 (t, J=6.3 Hz, 2H, ArCH$_2$C), 3.18 (t, J=5.5 Hz, 2H, ArCH$_2$C), 3.83 (t, J=5.5 Hz, 2H, OCH$_2$C), 3.88 (t, J=6 Hz, 2H, OCH$_2$C), 4.51 (s, 2H, OCH$_2$Ph), 6.86 (pair d, J=8.5 Hz, 1H, ArH), 6.92 (d, J=2 Hz, 1H, ArH), 7.25–7.40 (m, 6H, ArH+PhH), 9.1 (s, 1H, NH).

MS (m/z): 313 (M)$^+$, 282 (M-CH$_2$OH)$^+$, 91 (b.p., C$_7$H$_7$)$^+$.

EXAMPLE 6

Process A

Preparation of 1-Ethyl-7-fluoro-1,3,4,9-tetrahydro-8-(2-benzyloxyethyl)pyrano[3,4-b]indole-1-acetic Acid Methyl Ester (X: R$^1$=7-F, R=—C$_2$H$_5$, R$^3$=—CH$_3$, X=—CH$_2$Ph)

To a solution of 6-fluoro-7-(2-benzyloxyethyl)tryptophol (9.39 g, 30 mmole) and methyl 3-methoxy-2-pentenoate (4.32 g, 30 mmole) in methylene chloride (150 mL, dried over 4 Å sieves) at 0° C. was added dropwise over 5 minutes BF$_3$.Et$_2$O (4.25 g, 3.68 mL, d 1.154, 30 mmole). The dark solution was stirred in the cold for 10 minutes and then at room temperature for 2 hours. The mixture was cooled and washed to neutral with 5% NaHCO$_3$. The organic phase was washed with brine and dried (MgSO$_4$). Evaporation of the solvent yielded the crude title compound (quantitative yield) as a light brown oil. This material was used for the subsequent reaction without further purification.

$^1$H NMR (400 MHz, CDCl$_3$): δ0.71 (t, J=7.4 Hz, CCH$_3$), 1.86 (q, J=7.4 Hz, 2H, CCH$_2$C), 2.72 (m, 4H, ArCH$_2$C+CCH$_2$COO), 3.18 (m, 2H, ArCH$_2$C), 3.63 (s, 3H, OCH$_3$), 3.80 (t, J=6 Hz, 2H, OCH$_2$C), 3.88–4.02 (m, 2H, OCH$_2$C), 4.54 (s, 2H, OCH$_2$Ph), 6.84 (pair d, J=8.6 Hz, 1H, ArH), 7.27 (m, 6H, ArH+PhH), 9.31 (s, 1H, NH).

MS (m/z): 435 (M)$^+$, 396 (M-C$_2$H$_5$)$^+$, 352 (M-CH$_2$COOCH$_3$)$^+$, 91 (b.p., C$_7$H$_7$)$^+$.

EXAMPLE 7

Process A

Preparation of 1-Ethyl-7-fluoro-1,3,4,9-tetrahydro-8-(2-hydroxyethyl)pyrano[3,4-b]indole-1-acetic Acid Methyl Ester (XI: R$^1$=7-F, R=—C$_2$H$_5$, R$^3$=—CH$_3$)

To a solution of crude 1-ethyl-7-fluoro-1,3,4,9-tetrahydro-8-(2-benzyloxyethyl)pyrano[3,4-b]indole-1-acetic acid methyl ester (30 mmole) in a mixture of methanol (150 mL) and glacial acetic acid (50 mL), was added 10% Pd on charcoal (4 g) and the mixture was hydrogenated overnight at room temperature and atmospheric pressure. The catalyst was filtered off (Solka Floc) and the filtrate was evaporated to dryness. The resulting brown oil was dissolved in ether, the solution was neutralized with 5% NaHCO$_3$, washed with brine and dried (MgSO$_4$). Removal of the solvent yielded a brown foam that solidified upon standing (quantitative, crude yield). This material was used for the subsequent reaction without further purification. A sample was triturated with ether-petroleum ether yielding a white solid, m.p. 101°–103° C. (browning starts around 80° C.).

$^1$H NMR (400 MHz, CDCl$_3$): δ0.81 (t, J=7.4 Hz, 3H, CCH$_3$), 2.06 (m, 2H, CCH$_2$C), 2.75 (m, 2H, ArCH$_2$C), 2.94 (pair d, J=16 Hz, 2H, CCH$_2$COO), 3.13 (m, 2H, ArCH$_2$C), 3.7 (s, 3H, OCH$_3$), 3.98 (m, 4H, OCH$_2$C), 6.86 (pair d, J=8.6 Hz, 1H, ArH), 7.27 (m, 1H, ArH), 9.39 (broad s, 1H, NH).

MS (m/z, EI): 335 (M)+, 306 (M-C₂H₅)+, 262 (b.p., M-CH₂COOCH₃)+.

EXAMPLE 8

Process A

Preparation of
1-Ethyl-7-fluoro-1,3,4,9-tetrahydro-8-(2-oxoethyl)-pyrano[3,4-b]indole-1-acetic Acid Methyl Ester (XII: $R^1$=7-F, R=—C₂H₅, $R^3$=—CH₃)

To a solution of Dess-Martin periodinane (11.85 g, 97%, 27.13 mmole) in dry dichloromethane (100 mL, ex-4 Å sieves) kept under nitrogen was added dropwise a solution of the crude 1-ethyl-7-fluoro-1,3,4,9-tetrahydro-8-(2-hydroxyethyl)pyrano[3,4-b]indole-1-acetic acid methyl ester (20.87 mmole) in dry dichloromethane (80 mL). The reaction was complete after stirring at room temperature for 2 hours (aliquote worked-up, TLC, silica, hexane-EtOAc 1:1). The reaction mixture was diluted with ether (100 mL) and poured into saturated NaHCO₃ containing anhydrous sodium thiosulfate (30 g, 190 mmole). The mixture was stirred to dissolve the solids (about 10 minutes) and the layers were separated. The ether extract was washed with saturated NaHCO₃, brine and dried (MgSO₄). Removal of the solvent provided the title compound as a light brown oil that solidified in high vacuo (quantitative, crude yield).

This material was used for the subsequent reaction without further purification. An analytical sample was obtained by trituration of the crude product with ether to give pure product as a white solid, m.p. 94°–96° C. (dec.)

¹H NMR (400 MHz, CDCl₃): δ0.81 (t, J=7.3 Hz, 3H, CCH₃), 2.05 (m, 2H, CCH₂C), 2.73 (m, 2H, ArCH₂C), 2.94 (pair d, J=16.5 Hz, CCH₂COO), 3.74 (s, 3H, OCH₃), 3.98 (m, 4H, OCH₂C+CH₂CHO), 6.92 (pair d, J=8.5 Hz, 1H, ArH), 7.37 (m, 1H, ArH), 9.2 (s, 1H, NH), 9.75 (s, 1H, CHO).

MS (m/z, EI): 333 (M)+, 304 (M-C₂H₅)+, 260 (b.p., M-CH₂COOCH₃)+.

Anal. Calcd. for C₁₈H₂₀FNO₄: C, 64.85; H, 6.05; N, 4.20%. Found: C, 64.48; H, 5.96; N, 4.12%.

EXAMPLE 9

Process A

Preparation of
1-Ethyl-7-fluoro-1,3,4,9-tetrahydro-8-(2-propenyl)-pyrano[3,4-b]indole-1-acetic Acid Methyl Ester (XIII: $R^1$=7-F, R=—C₂H₅, $R^3$=—CH₃)

According to the procedure of L. Lombardo, Org. Syntheses Vol. 65, 81, in a 500 mL 3-neck flask equipped with a mechanical stirrer, nitrogen inlet and rubber septum was placed zinc dust (325 mesh, 6.47 g, 99 mmole) anhydrous THF (70 mL) and dibromomethane (5.64 g, 2.27 mL, d 2.477, 32.44 mmole). The mixture was cooled with stirring to −40° C. (bath temperature) under nitrogen. Titanium (IV) chloride (4.39 g, 2.54 mL, d 1.73, 23.14 mmole) was carefully added (via syringe) over 10 minutes. After an additional 10 minutes the cooling bath was removed and the flask was placed in a Dewar containing ice-water (bath temperature 0°–2° C.). The mixture was gently stirred for three days at 0°–2° C. The dark grey slurry was diluted at 0° C. with dry dichloromethane (20 mL, ex-4 Å sieves).

A solution of the crude 1-ethyl-7-fluoro-1,3,4,9-tetrahydro-8-(2-oxoethyl)pyrano[3,4-b]indole-1-acetic acid methyl ester (20.87 mmole) in dry dichloromethane was added dropwise under nitrogen over 30 minutes. After stirring an additional 90 minutes at 0° C. no aldehyde was present (aliquote worked-up, TLC, silica, hexane-EtOAc 1:1). After 110 minutes a slurry of NaHCO₃ (32 g) in water (16 mL) was added cautiously over 30 minutes with gentle stirring (heavy foaming). The final pH was adjusted to 8 with saturated NaHCO₃ as needed. The insolubles were removed by filtration (Celite) and washed with CH₂Cl₂. The combined filtrates were separated and the organic layer was dried over MgSO₄ containing NaHCO₃ (5 g). The organic solution was shaken with the drying agent for 10–15 minutes to remove last traces of titanium salts. Removal of the solvent yielded a pale yellow syrup that was purified by quick filtration over a short silica column using dichloromethane as eluant affording 4.64 g of product as a pale yellow syrup that solidified upon standing (67% yield).

¹H NMR (400 MHz, CDCl₃): δ0.81 (t, J=7.3 Hz, 3H, CCH₃), 2.06 (m, 2H, CCH₂C), 2.75 (m, 2H, ArCH₂C), 2.94 (pair d, J=16.7 Hz, 2H, CCH₂COO), 3.64 (t, J=7 Hz, 2H, ArCH₂C=C), 3.71 (s, 3H, OCH₃), 3.98 (m, 2H, OCH₂C), 5.12 (pair d, 1H, CH₂C=), 5.25 (pair d, 1H, CH₂C=), 5.95 (m, 1H, C=CH), 6.86 (pair d, J=8.5 Hz, 1H, ArH), 7.78 (m, 1H, ArH), 9.15 (s, 1H, NH).

MS (m/z, EI): 331 (M)+, 302 (M-C₂H₅)+, 258 (b.p., M-CH₂COOCH₃)+.

EXAMPLE 10

Process A

Preparation of
1-Ethyl-7-fluoro-1,3,4,9-tetrahydro-8-(2-propenyl)-pyrano[3,4-b]indole-1-acetic Acid Methyl Ester (XII: $R^1$=7-F, R=—C₂H₅, $R^3$=—CH₃)

According to the procedure of M. Schlosser et al, Chimia, 36, 396 (1982) anhydrous THF (2.5 mL) was placed in a flame dried flask. A mixture of triphenylphosphonium bromide and sodium amide (0.125 g, 0.3 mmol) was added under nitrogen and the mixture stirred for 20 minutes at room temperature. The yellow solution of the ylid was cooled to −78° C. and treated dropwise over 20 minutes with a solution of 1-ethyl-7-fluoro-1,3,4,9-tetrahydro-8-(2-oxoethyl)pyrano[3,4-b]indole-1-acetic acid methyl ester (0.1 g, 0.3 mmol, prepared according to the process of Example 8) in 1.5 mL of dry THF. After 0.5 hours at −78° C., the reaction mixture was allowed to warm to room temperature and stirring was continued overnight. The reaction mixture was concentrated in vacuo and the residue triturated with Et₂O. The solids were filtered and the filtrate evaporated to give a yellow oil (0.170 g). The crude product was purified by flash chromatography (silica Merck 60, methylene chloride) to give 0.011 g of the title compound (11%, white solid).

¹H NMR (CDCl₃, 200 MHz): δ0.81 (t, 3H, CH₃CH₂C), 2.06 (m, 2H, CCH₂CH₃), 2.68–2.84 (m, 2H,

ArCH₂C), 2.94 (dd, 2H, CCH₂CO), 3.64 (t, 2H, CH₂—CH=CH₂), 3.71 (s, 3H, OCH₃), 3.89–4.06 (m, 2H, OCHC), 5.12 (dd, 1H, J=1.4 Hz, vinyl), 5.25 (dd, 1H, vinyl), 5.95 (m, 1H, vinyl), 6.86 (dd, 1H, ArH), 7.28 (m, 1H, ArH), 9.11 (s, 1H, NH).

EXAMPLE 11

Process A

Preparation of 1-Ethyl-7-fluoro-1,3,4,9-tetrahydro-8-(2-propenyl)-pyrano[3,4-b]indole-1-acetic Acid Methyl Ester (XIII: $R^1$=7-F, R=—C₂H₅, $R^3$=—CH₃)

Step 1. Preparation of 1-Ethyl-7-fluoro-1,3,4,9-tetrahydro-8-(2-hydroxy-3-trimethylsilylpropyl)pyrano[3,4-b]indole-1-acetic Acid Methyl Ester According to the procedure of T. H. Chan et al, J. Org. Chem., 39, 3264 (1974) an ethereal solution of trimethylsilylmethyl magnesium chloride (1.9M, 0.85 mL, 1.6 mmol) was placed in a flame dried flask and treated dropwise under nitrogen with a solution of 1-ethyl-7-fluoro-1,3,4,9-tetrahydro-8-(2-oxoethyl)-pyrano[3,4-b]-indole-1-acetic acid methyl ester (0.48 g, 1.44 mmol, prepared according to the process of Example 8) in 4 mL of Et₂O. An orange precipitate formed immediately. The mixture was heated at reflux for 1 hour, cooled and treated with 4 mL of saturated NH₄Cl solution. The layers were separated and the organic phase was washed with brine (5 mL). After drying (Na₂SO₄), the solvent was evaporated to give the crude product as a yellow oil (0.580 g) that was used in the subsequent reaction without further purification.

MS (m/z, EI): 421 (M+), 348 (M-TMS)+, 304 (M-CHOHCH₂TMS)+, 231 (304-CH₂CO₂CH₃)+, 73 (b.p., TMS).

Step 2. Preparation of 1-Ethyl-7-fluoro-1,3,4,9-tetrahydro-8-(2-propenyl)pyrano[3,4-b]indole-1-acetic Acid Methyl Ester According to the procedure of R. F. Hurdlik et al, J. Am. Chem. Soc., 97, 1464 (1975) to an ice-cold solution of 1-ethyl-7-fluoro-1,3,4,9-tetrahydro-8-(2-hydroxy-3-trimethylsilylpropyl)pyrano[3,4-b]indole-1-acetic acid methyl ester (crude material, 0.5 g, prepared as described in Step 1) in 20 mL of dry CH₂Cl₂, was added 0.125 mL of boron trifluoride etherate. The mixture was stirred for 1 hour at 0° C., washed with saturated NaHCO₃ and dried (Na₂SO₄). Removal of the solvent afforded 0.480 g of crude product. Purification of this material by flash chromatography (silica Merck 60, methylene chloride) provided pure product (82 mg, 17%, white solid).

¹H NMR (CDCl₃, 200 MHz): δ0.81 (t, 3H, CH₃CH₂C), 2.06 (m, 2H, CCH₂CH₃), 2.68–2.84 (m, 2H, ArCH₂C), 2.94 (dd, 2H, CCH₂CO), 3.64 (t, 2H, CH₂—CH=CH₂), 3.71 (s, 3H, OCH₃), 3.89–4.06 (m, 2H, OCH₂C), 5.12 (dd, 1H, J=1.4 Hz, vinyl), 5.25 (dd, 1H, J=1.5 Hz, vinyl), 5.9 (q, 1H, vinyl), 6.86 (dd, 1H, ArH), 7.28 (m, 1H, ArH), 9.11 (s, 1H, NH).

MS (m/z, EI): 331 (M)+, 302 (M-C₂H₅)+, 258 (M-CH₂COOCH₃, b.p.)+.

EXAMPLE 12

Process A

Preparation of 1-Ethyl-7-fluoro-1,3,4,9-tetrahydro-8-(2-propenyl)-pyrano[3,4-b]indole-1-acetic Acid (I: $R^1$=7-F, R=—C₂H₅, $R^2$=—H)

A solution of 1-ethyl-7-fluoro-1,3,4,9-tetrahydro-8-(2-propenyl)pyrano[3,4-b]indole-1-acetic acid methyl ester (2.1 g, 6.34 mmol) in a mixture of methanol (20 mL) and water (20 mL) containing 2.1 g (15 mmol) of K₂CO₃ was heated at reflux under nitrogen for 1.5 hours. The methanol was removed in vacuo and the residue was diluted with water (50 mL) and acidified in the cold to pH 3 with concentrated HCl. The mixture was extracted with ether and the extracts were dried (Na₂SO₄) and evaporated to yield a pale yellow oil (quantitative yield, homogeneous in TLC) that set up on standing. One recrystallization from CH₂Cl₂-hexane provided pure title compound (white solid, 1.55 g, 74%, m.p. 123°–124° C.). A second crop was obtained by further concentrating the mother liquors.

¹H NMR (CDCl₃, 200 MHz): δ0.84 (t, 3H, CH₃CH₂C), 2.05 (m, 2H, CCH₂CH₃), 2.78 (dt, 2H, ArCH₂C), 3.0 (dd, 2H, CCH₂CO), 3.6 (d, 2H, ArCH₂CH), 4.04 (m, 2H, OCH₂C), 5.12 (m, 2H, vinyl), 5.95 (q, 1H, vinyl), 6.88 (dd, 1H, ArH), 7.28 (m, 1H, ArH), 8.70 (s, 1H, NH).

Anal. Calcd. for C₁₈H₂₀FNO₃: C, 68.20; H, 6.36; N, 4.42%. Found: C, 68.17; H, 6.42; N, 4.32%.

We claim:

1. A process for producing compounds of formula (I)

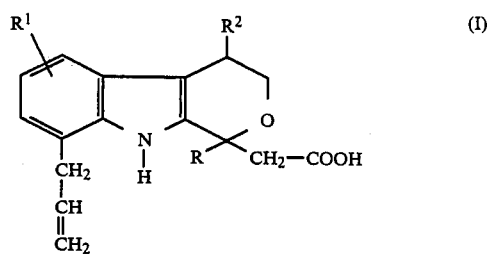

wherein R is lower alkyl containing 1 to 4 carbon atoms; $R^1$ is hydrogen, lower alkyl containing 1 to 4 carbon atoms, or halogen; $R^2$ is hydrogen and the pharmaceutically acceptable salts thereof which comprises the steps (a) successively benzylating and reducing substituted 2-nitrophenethyl alcohols of structure (III)

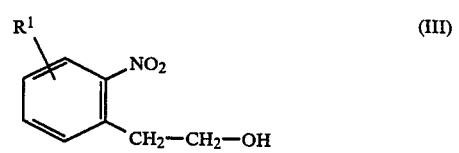

wherein $R^1$ is as defined above to produce the substituted amine of structure (VI)

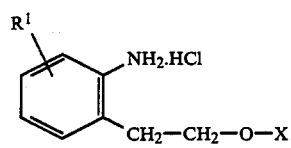
(VI)

wherein $R^1$ is as defined above and X is benzyl (b) reacting said amine (VI) with $HNO_2$ and $SnCl_2$ to produce the substituted hydrazine of formula (VII)

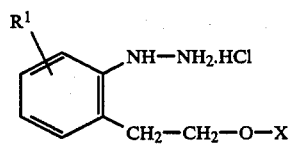
(VII)

wherein $R^1$ and X are as defined above (c) reacting said hydrazine (VII) with dihydrofuran to produce the corresponding hydrazone and in the presence of zinc chloride converting the hydrazone to the corresponding tryptophol of structure (VIII)

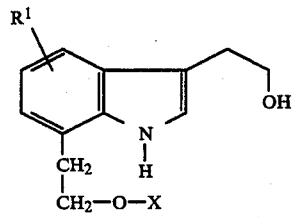
(VIII)

wherein $R^1$ and X are as defined above (d) reacting said tryptophol of formula (VIII) with 3-oxo-2-alkanoic acid alkyl ester of formula (IX)

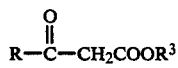
(IX)

wherein R is as defined above and $R^3$ is lower alkyl containing 1 to 8 carbon atoms to produce the indole alkyl ester of formula (X)

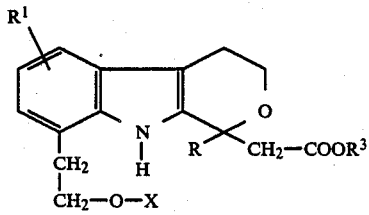
(X)

wherein R, $R^1$, $R^3$ and X are as defined above (e) reducing said indole (X) to produce the hydroxy ester of formula (XI)

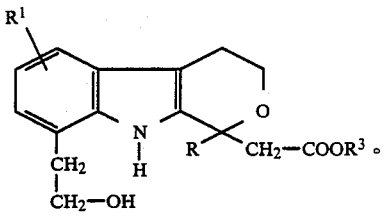
(XI)

wherein R, $R^1$ and $R^3$ are as defined above (f) oxidizing said hydroxy ester (XI) to produce the oxo ester of structure (XII)

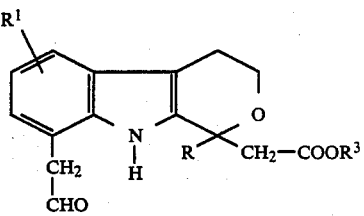
(XII)

wherein R, $R^1$ and $R^3$ are as defined above (g) methylenating said oxo ester (XII) to produce the ester of structure (XIII)

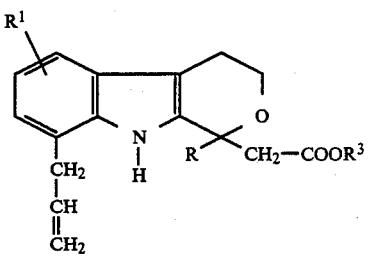
(XIII)

wherein R, $R^1$ and $R^3$ are as defined above (h) hydrolyzing said ester to produce the desired compound of structure (I) and optionally converting said compound to a pharmaceutically acceptable salt.

2. The process according to claim 1 wherein R is ethyl, $R^1$ is fluoro and $R^2$ is hydrogen.

3. The process according to claim 1 wherein in step (d) said 3-oxo-2-alkanoic acid alkyl ester is methylpropionyl acetate and the reaction is carried out in the presence of boron trifluoride etherate.

4. The process according to claim 1 wherein in step (e) the hydrogenation of the ester of structure (X) is carried out with hydrogen in the presence of 10% Pd-C at atmospheric pressure and room temperature.

5. The process according to claim 1 wherein in step (f) the oxidation of the hydroxy ester of formula (XI) is carried out with Dess-Martin periodinane in dichloromethane.

6. The process according to claim 1 wherein in step (g) the methylenation of the oxo ester of structure (XII) is carried out with the reagent prepared from zinc dust, methylene bromide, THF and $TiCl_4$ at 0° C.

7. The process according to claim 1 wherein in step (g) the methylenation of the oxo ester of structure (XII) is carried out by reaction with trimethylsilyl methyl magnesium chloride followed by treatment of the intermediate adduct with boron trifluoride etherate.

8. A process according to claim 1 wherein in step (g) the methylenation of the oxo ester of structure (XII) is carried out by reaction with an ylid generated from methyltriphenyl phosphonium bromide and sodium amide or phenyllithium in THF.

9. A process for producing compounds of formula (I)

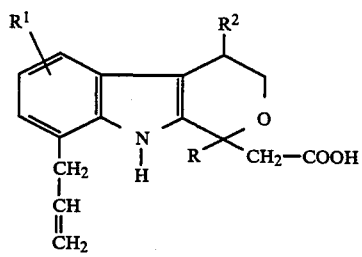
(I)

wherein R is lower alkyl containing 1 to 4 carbon atoms; $R^1$ is hydrogen, lower alkyl containing 1 to 4 carbon atoms, or halogen; $R^2$ is hydrogen and the pharmaceutically acceptable salts thereof which comprises the steps (a) acylating a substituted tryptophol of structure (VIII)

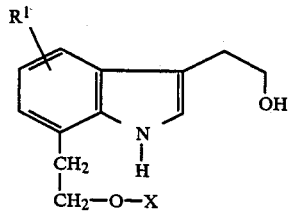
(VIII)

wherein $R^1$ is as defined above and X is benzyl to produce the substituted tryptophol of formula (XV)

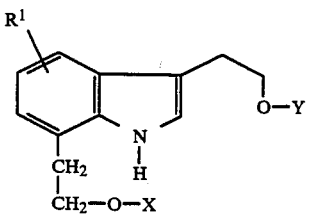
(XV)

wherein $R^1$ and X are as defined above and Y is acetyl (b) reducing said tryptophol of formula (XV) to the substituted tryptophol of formula (XVI)

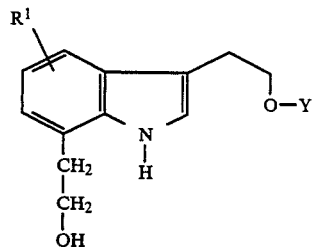
(XVI)

wherein $R^1$ and Y are as defined above (c) oxidizing said tryptophol of formula (XVI) to the oxo tryptophol of formula (XVII)

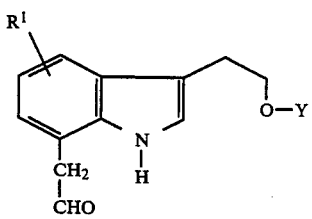
(XVII)

wherein $R^1$ and Y are as defined above (d) methylenating said oxo tryptophol (XVII) to produce the substituted tryptophol of formula (XVIII)

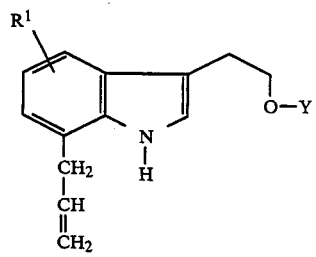
(XVIII)

wherein $R^1$ and Y are as defined above (e) hydrolyzing said tryptophol of structure (XVIII) to provide the substituted tryptophol of structure (XIX)

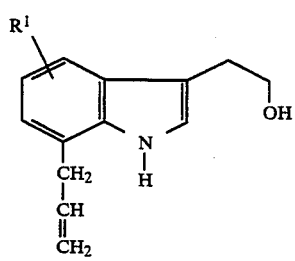
(XIX)

wherein $R^1$ is as defined above (f) reacting said tryptophol of formula (XIX) with 3-oxo-2-alkanoic acid, alkyl ester of formula (IX)

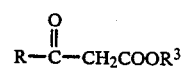
(IX)

wherein R is as defined above and $R^3$ is lower alkyl containing 1 to 8 carbon atoms to produce the alkyl ester of formula (XIII)

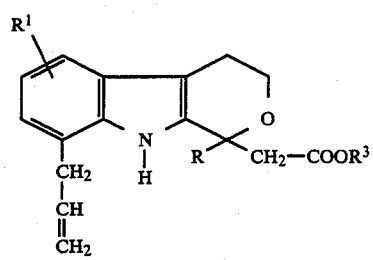
(XIII)

wherein R, $R^1$ and $R^3$ are as defined above (g) hydrolyzing said ester to produce the desired compounds of structure (I) and optionally converting said compound to a pharmaceutically acceptable salt.

10. The process according to claim 9 wherein in step (b) the hydrogenation of the tryptophol of structure (XV) is carried out in the presence of 10% Pd-C at atmospheric pressure and room temperature.

11. The process according to claim 9 wherein in step (c) the oxidation of the tryptophol of structure (XVI) is carried out with Dess-Martin periodinane in dichloromethane.

12. The process according to claim 9 wherein in step (d) the methylenation of oxo tryptophol of formula (XVII) is carried out with the reagent prepared from zinc dust, methylene bromide, THF and $TiCl_4$ at 0° C.

13. The process according to claim 9 wherein in step (d) the methylenation of the oxo tryptophol of structure (XVII) is carried out by reaction with trimethylsilyl methyl magnesium chloride followed by treatment of the intermediate adduct with boron trifluoride etherate.

14. A process according to claim 9 wherein in step (d) the methylenation of the oxo tryptophol of structure (XVII) is carried out by reaction with an ylid generated from methyltriphenyl phosphonium bromide and sodium amide or phenyllithium in THF.

15. A process for producing compounds of formula (I)

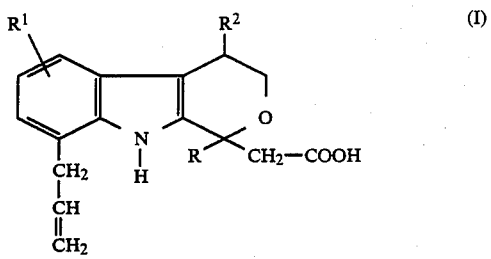
(I)

wherein R is lower alkyl comprising 1 to 4 carbon atoms; $R^1$ is hydrogen, lower alkyl containing 1 to 4 carbon atoms, or halogen; $R^2$ is lower alkyl containing 1 to 4 carbon atoms and the pharmaceutically acceptable salts thereof which comprises the steps (a) alkylating isatins of formula (XX)

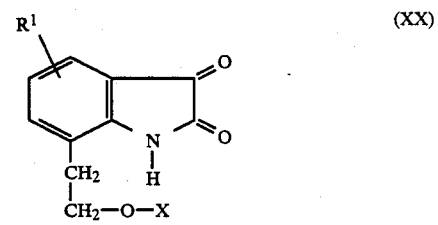
(XX)

wherein $R^1$ is as defined above and X is benzyl to produce the tryptophol of formula (XXII)

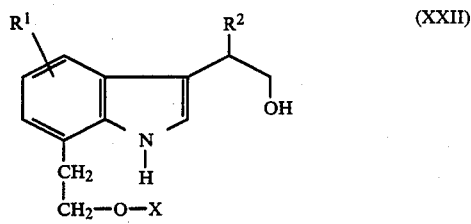
(XXII)

wherein $R^1$, $R^2$ and X are as defined above
(b) reacting said tryptophol of structure (XXII) with 3-oxo-2-alkanoic acid alkyl ester of formula (IX)

(IX)

wherein R is as defined above and $R^3$ is lower alkyl containing 1 to 8 carbon atoms to produce the alkyl ester of formula (XXIII)

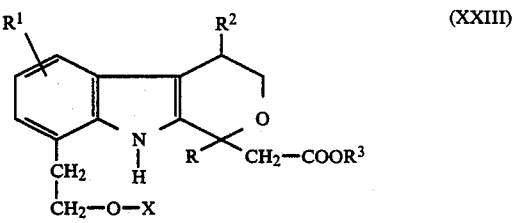
(XXIII)

wherein R, $R^1$, $R^2$, $R^3$ and X are as defined above
(c) successively hydrogenating, oxidizing, methylenating and hydrolyzing said compound of formula (XXIII) to produce compounds of formula (I) and optionally converting said compound to a pharmaceutically acceptable salt.

* * * * *